(12) United States Patent
Chen et al.

(10) Patent No.: US 9,387,117 B2
(45) Date of Patent: Jul. 12, 2016

(54) NEGATIVE PRESSURE ORAL APPARATUS

(75) Inventors: Chung-Chu Chen, Hsinchu (TW);
Ching Shang, Palo Alto, CA (US);
Marina Sirota, San Francisco, CA (US);
Zhen Yao, Stanford, CA (US)

(73) Assignee: Somnics, Inc., San Jose, CA (US)

( * ) Notice: Subject to any disclaimer, the term of this patent is extended or adjusted under 35 U.S.C. 154(b) by 283 days.

(21) Appl. No.: 12/891,398

(22) Filed: Sep. 27, 2010

(65) Prior Publication Data
US 2011/0073119 A1  Mar. 31, 2011

Related U.S. Application Data

(60) Provisional application No. 61/277,753, filed on Sep. 28, 2009.

(51) Int. Cl.
*A61F 5/56* (2006.01)
*A61M 16/04* (2006.01)
(Continued)

(52) U.S. Cl.
CPC . *A61F 5/566* (2013.01); *A61F 5/56* (2013.01); *A61M 1/0023* (2013.01); *A61M 16/0488* (2013.01); *A61C 17/04* (2013.01)

(58) Field of Classification Search
CPC ......... A61F 5/56; A61F 5/566; A63B 71/085; A61C 7/08; A61C 17/04; A61C 17/043; A61C 7/00; A61M 1/00; A61M 1/0023; A61M 1/0058; A61M 16/0488; A61M 16/049; A61M 16/0497
USPC ......... 128/848, 859, 861, 862, 205.19; 433/6, 433/91–96
See application file for complete search history.

(56) References Cited

U.S. PATENT DOCUMENTS

| 5,626,128 A | 5/1997 | Bradley et al. |
| 5,957,133 A | 9/1999 | Hart |

(Continued)

FOREIGN PATENT DOCUMENTS

WO  WO 2009/035325 A1  3/2009

OTHER PUBLICATIONS

"Obstructive Sleep Apnea", Access Medicine, Harrison's Principles of Internal Medicine, Chapter 259, 17th Edition, pp. 1-7.
(Continued)

*Primary Examiner* — Keri J Nelson
(74) *Attorney, Agent, or Firm* — Senniger Powers LLP

(57) ABSTRACT

This invention provides an oral apparatus and method capable of alleviating or curing snore and obstructive sleep apnea by applying a negative pressure through a mini oral interface to the oral cavity. The mini oral interface creates a secure connection between the interface and mouth or teeth and prevents the interface from falling off. The oral interface also provides fixation between upper and lower lips (or tooth) and prevents opening of patient's mouth during sleeping. The negative pressure pulls the tongue toward upper palate and also pulls the soft palate forward as well. By moving the tongue and the soft palate in a forward direction, the patency of the upper airway near the pharynx is maintained to prevent sleep-disordered breathing. The negative pressure will pull the lips inward to close the mouth ad prevent air from entering the oral cavity from atmosphere. The negative pressure will also pull the soft palate into contact with the rear surface of the tongue to create a seal that prevents the air from entering the oral cavity through the nasal airway.

32 Claims, 23 Drawing Sheets

(51) Int. Cl.
  *A61M 1/00* (2006.01)
  *A61C 17/06* (2006.01)

(56) References Cited

U.S. PATENT DOCUMENTS

| | | | |
|---|---|---|---|
| 2002/0033175 | A1 | 3/2002 | Bateman et al. |
| 2003/0121520 | A1 | 7/2003 | Parker et al. |
| 2003/0143512 | A1 | 7/2003 | Hirsch et al. |
| 2004/0194787 | A1* | 10/2004 | Miller ........................ 128/848 |
| 2005/0066976 | A1 | 3/2005 | Wondka |
| 2005/0166928 | A1 | 8/2005 | Jiang |
| 2006/0096600 | A1 | 5/2006 | Witt et al. |
| 2007/0277818 | A1* | 12/2007 | Chen ....................... 128/200.24 |
| 2007/0295335 | A1 | 12/2007 | Nashed |
| 2008/0318183 | A1* | 12/2008 | Suzman ........................ 433/93 |
| 2009/0120446 | A1 | 5/2009 | Vaska et al. |

OTHER PUBLICATIONS

Damjanovic et al., "Compliance in sleep apnoea therapy: influence of home care support and pressure mode", European Respiratory Journal, vol. 33, No. 4, Jan. 7, 2009, pp. 804-811.

Ferguson et al., "Oral Appliances for Snoring and Obstructive Sleep Apnea: A Review", Sleep, vol. 29, No. 2, 2006, pp. 244-262.

Flemons, "Obstructive Sleep Apnea", The New England Journal of Medicine, vol. 347, No. 7, Aug. 15, 2002, pp. 498-504.

Giles TL et al., "Continuous positive airways pressure for obstructive sleep apnoea in adults (Review)", The Cochrane Library 2006, Issue 2, pp. 1-80.

Gotsopoulos et al., "Oral Appliance Therapy Improves Symptoms in Obstructive Sleep Apnea", Am J Respir Crit Care Med, vol. 166, 2002, pp. 743-748.

Haentjens et al., "The Impact of Continuous Positive Airway Pressure on Blood Pressure in Patients With Obstructive Sleep Apnea Syndrome", Arch Intern Med, vol. 167, Apr. 23, 2007, pp. 757-765.

Hoy et al., "Can Intensive Support Improve Continuous Positive Airway Pressure Use in Patients with the Sleep Apnea/Hypopnea Syndrome?", Am J Respir Crit Care Med, vol. 159, 1999, pp. 1096-1100.

Kerr et al., "The Physiological Regulation of Salivary Secretions in Man", Proceedings of the Royal Society of Medicine, pp. 334.

Lawati et al., "Epidemiology, Risk Factors, and Consequences of Obstructive Sleep Apnea and Short Sleep Duration", Progress in Cardiovascular Diseases, vol. 51, No. 4, 2009, pp. 285-293.

Mackie et al., "Mastication and its Influence on Human Salivary Flow and Alpha-Amylase Secretion", Physiology & Behavior, vol. 47, 1990, pp. 593-595.

Sucena et al., "Continuous positive airway pressure treatment for sleep apnoea: compliance increases with time in continuing users", European Respiratory Journal, vol. 27, No. 4, 2006, pp. 761-766.

Sundaram S et al., "Surgery for obstructive sleep apnoea in adults (Review)", The Cochrane Library 2009, Issue 1, pp. 1-72.

Won et al., "Surgical Treatment of Obstructive Sleep Apnea", Proc Am Thorac Soc, vol. 5, 2008, pp. 193-199.

Young et al., "Risk Factors for Obstructive Sleep Apnea in Adults", American Medical Association, vol. 291, No. 16, Apr. 28, 2004, pp. 2013-2016.

Young et al., "The Occurence of Sleep-Disordered Breathing Among Middle-Aged Adults", The New England Journal of Medicine, vol. 328, No. 17, Apr. 29, 1993, pp. 1230-1235.

* cited by examiner

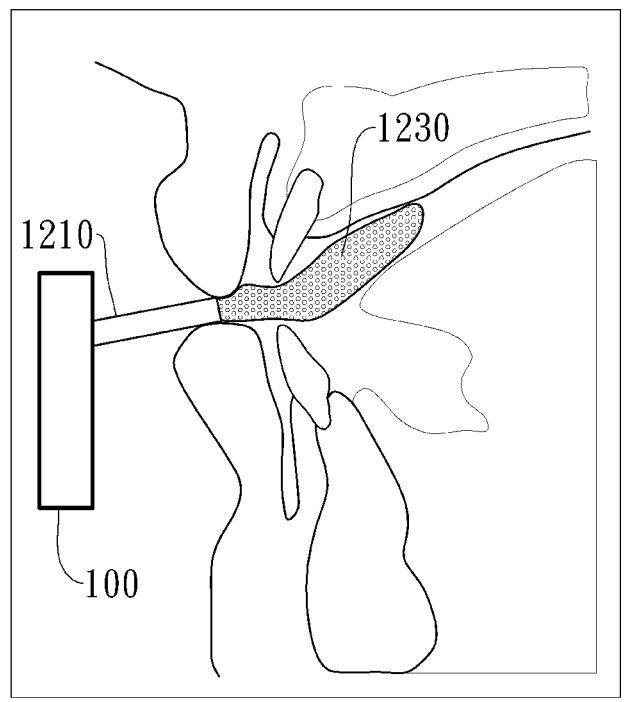
Fig. 12A
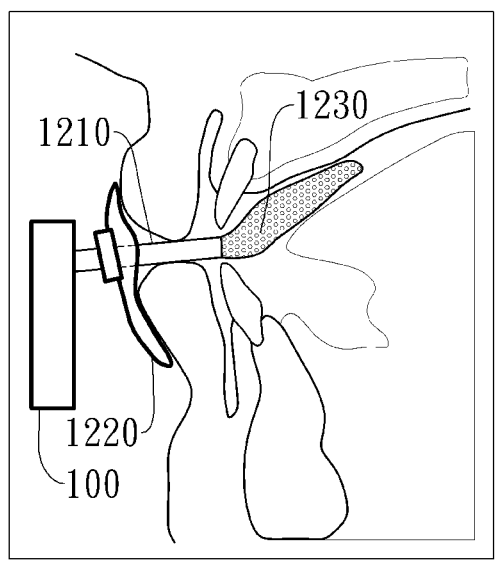 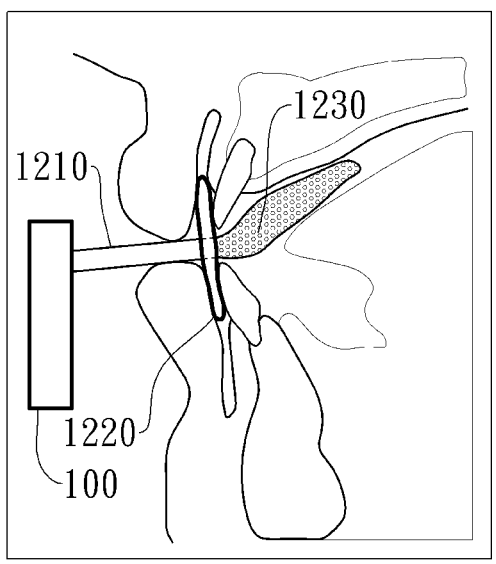
Fig. 12B                Fig. 12C

NEGATIVE PRESSURE ORAL APPARATUS

CROSS REFERENCE TO RELATED APPLICATIONS

This nonprovisional application claims the benefit of U.S. Provisional Application No. 61/277,753 filed on Sep. 28, 2009. The entire contents of the above application is hereby incorporated by reference.

BACKGROUND OF THE INVENTION

1. Field of the Invention

The present invention is related to oral apparatus and methods capable of alleviating or curing snoring and obstruction of upper airway in obstructive sleep apnea (OSA) and snore patients. More particularly, the present invention relates to a negative pressure oral apparatus disposed in the oral cavity.

2. Prior Art

Obstructive sleep apnea (OSA) is a condition in which repeated collapses in the patient's airway during inhalation causes a cessation of breathing during sleep. During inhalation, air pressure in the lungs and respiratory passages is reduced. If during this time, the tone of the muscles in the upper-airway is reduced, the airway tends to collapse. As the airway begins to occlude prior to an apnea, the patient often begins to snore. Snoring is an effort to try to combat the collapsed airway. These obstructions occur in different locations along the respiratory pathway in different patients, but the two common locations are the oropharynx or the nasopharynx.

People with moderate to severe OSA experience daytime sleepiness, fatigue, and poor concentration. In addition to these immediate problems, research has shown that patients with OSA use more medical resources, have an increased risk of medical disability, and finally have a higher mortality rate. Patients with severe OSA are estimated to have a three to six fold increased risk of mortality considering all causes. OSA is also implicated in many cardiovascular conditions, such as systemic hypertension and some degree of pulmonary hypertension. It is associated with an increased risk for myocardial infarction, cerebrovascular disease, and cardiac arrhythmia. OSA also causes excessive daytime sleepiness due to interrupted sleeping pattern at night which leads to inability to concentrate. Patients' daily functions are impaired as their neuro-cognitive function is compromised. They are more likely to make errors and run into accidents. Therefore, OSA is a significant medical condition with serious negative outcomes if left untreated.

There are several current treatment options for OSA patients. Oral appliance is used to treat mild OSA, but they often don't work well and cause damage to gums and teeth. Several types of surgery are used to treat OSA, however, surgical options are invasive, expensive and painful with recovery periods up to 6 months. The most common treatment for moderate to severe sleep apnea in adults is CPAP, which has 96% market share in OSA therapeutics. A CPAP machine consists of a mask, a pump and a humidifier. The device continuously blows pressurized air into the patient's nose to keep the airway open during sleep. CPAP is quite effective, however, it has unpleasant side effects such as dry throat and nose congestion. Patients who use CPAP often feel bloated in the morning and experience headaches. The machine is noisy and uncomfortable for the user and their partner. CPAP is currently the first-line and gold standard treatment, but it suffers low compliance due to significant side effects.

It has been proposed to apply a negative pressure to the patient's oral cavity to pull the tongue and soft palate forward to maintain the patency of the airway, as an improvement over CPAP, for example, U.S. Pat. No. 5,957,133, Patent Publication No. 2005/0166928, and 2006/0096600. While promising in theory, these prior arts comprise relatively large structures to engage the teeth and/or to retain the tongue. Moreover, negative pressure is applied directly on the soft tissues of the tongue to hold the tongue within the cavity. However, these approaches tend to occupy a lot of space in the oral cavity, which may cause discomfort and damage to large area of teeth, gum, and soft tissues. At the same time, the presence of such larger devices may induce excess saliva secretion and elicit the gag reflex. The other major disadvantage of these approaches also includes that the oral devices are anatomically dependent, that they required special technicians to customize the interface for each individual patient.

Therefore, it is one object of the present invention to provide alternative and improved methods and apparatus for treating obstructive sleep apnea and snoring. It is another object of the present invention to provide minimally intrusive methods and apparatus with components that are comfortable and convenient to use. It is still another object of the present invention to provide methods and apparatus that avoid contacting the portions of the oral cavity that cause discomfort, induce excess saliva, and trigger the gag reflex. The methods and apparatus should also be simple to implement and be effective to significantly improve patency of a patient's airway during sleep. At least some of these objectives will be met by the inventions described hereinafter.

SUMMARY OF THE INVENTION

The present invention provides an oral apparatus and method capable of alleviating or curing snore and obstructive sleep apnea by creating a mini oral interface and applying negative pressure through the mini interface to the oral cavity. The mini interface includes a first fixation part, which creates a secure connection to mouth or teeth and prevents falling-off from patient's mouth during sleep. The mini oral interface may also include a second fixation part, which fixes the relative position of the upper and lower lips, jaws, or teeth and helps the patient close mouth during sleep. The negative pressure pulls the tongue toward upper palate and also pulls the soft palate forward as well. By moving the tongue and the soft in a forward direction, the patency of the upper airway near the pharynx is maintained to prevent sleep-disordered breathing. The negative pressure will pull the lips inward to close the mouth and prevent air from entering the oral cavity from atmosphere. The negative pressure will also pull the soft palate into contact with the rear surface of the tongue to create a seal that prevents the air entering the oral cavity through the nasal airway. This therapy only required partial pump-on time and minimal airflow, which is very energy-efficient and quiet.

In one embodiment, the present invention provides an oral apparatus, comprising: a fixation part, which can be attached on teeth permanently or semi-permanently; an air conduit with a complementary part which can be interlocked with said fixation part temporarily; the air conduit has a first opening connecting to the fixation part; the air conduit also has a second opening which can be connected to a negative pressure source.

In another embodiment, the present invention provides a method, comprising: attaching a fixation part on teeth permanently or semi-permanently; providing an air conduit with a complementary part which interlocks with said fixation part; applying a negative pressure to oral cavity via said air conduit.

In another embodiment, the present invention provides an oral apparatus, comprising: a fixation part which is a lip interface and an air conduit; the lip interface adheres to at least one side of the lips, and does not cover the mouth completely; the air conduit has a first opening connecting to the lip interface and extending into the oral cavity; the air conduit also has a second opening which can be connected to a negative pressure source.

In another embodiment, the present invention provides an oral apparatus, comprising: a fixation part which is a porous interface and an air conduit; the porous interface is inserted into the users' oral cavity; the air conduit has a first opening connecting to the porous interface the air conduit also has a second opening which can be connected to a negative pressure source.

In yet another embodiment, the present invention provides an oral apparatus, comprising: a fixation part which is a mask and an air conduit; the mask covers the user's mouth and lower jaw; the mask has two straps (earbands or headbands) that secure the mask and the air conduct. The air conduit has a first opening connecting to the porous interface and extending into the oral cavity; the air conduit also has a second opening which can be connected to a negative pressure source.

In still another embodiment, the present invention provides an oral apparatus, comprising: a fixation part which is a head belt and an air conduit; the head belt has a head supporting part placed on top of the head and also a jaw supporting part placed under the chin; The head belt helps to secure the air conduit and also prevents the mouth from opening. The air conduit has a first opening connecting to the jaw supporting part and extending into the oral cavity; the air conduit also has a second opening which can be connected to a negative pressure source.

BRIEF DESCRIPTION OF THE DRAWINGS

The objects, spirits and advantages of the preferred embodiments of the present invention will be readily understood by the accompanying drawings and detailed descriptions, wherein:

FIG. 12A shows a schematic diagram of an oral apparatus according to the twelfth embodiment of the present invention;

FIG. 12B to FIG. 12E show variations of the twelfth embodiment of the present invention;

DETAILED DESCRIPTION OF PREFERRED EMBODIMENTS OF THE INVENTION

Figure 1A:
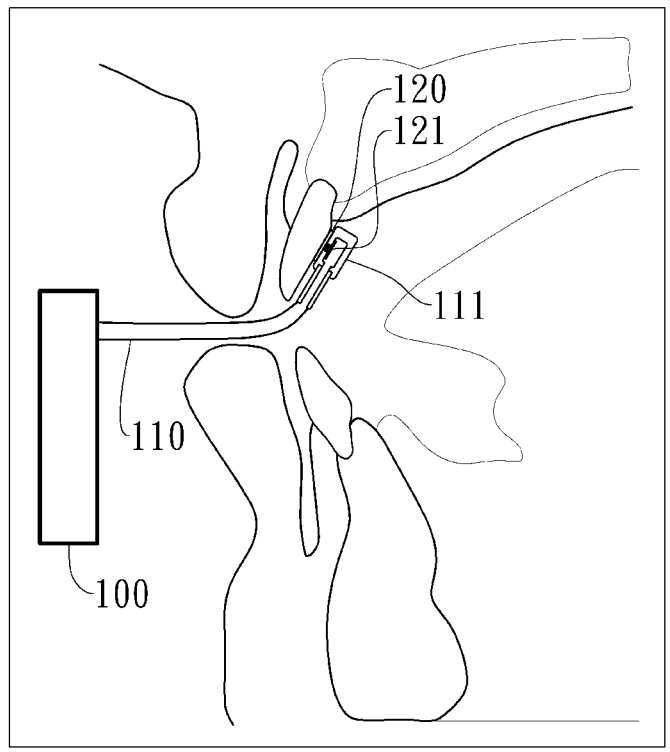
FIG. 1A and FIG. 1B show schematic diagrams of an oral apparatus according to the first embodiment of the present invention.

Reference will now be made in detail to the present exemplary embodiments, examples of which are illustrated in the accompanying drawings. Wherever possible, the same reference numbers are used in the drawings and the description to refer to the same or like parts.

FIG. 1A is a cross-section view of a negative pressure oral apparatus according to a first embodiment of the present invention. The negative pressure oral apparatus comprises a fluid conduit 110, a fixation par which is a tooth pairing part 120, and a conduit pairing part 111 near the end of the fluid conduit 110. The tooth paring part 120 can be attached to the surface of teeth by gluing or bonding permanently or temporarily. The tooth pairing part 120 has a pairing structure 121 which can be physically connected and disconnected with the conduit paring part 111. Once the tooth paring part 120 and conduit pairing part 111 are physically connected, a negative pressure source 100 can draw air out of oral cavity and thus produce a negative pressure environment to pull the tongue, soft palate and other soft tissue forward to maintain the airway patency.

Figure 1B:
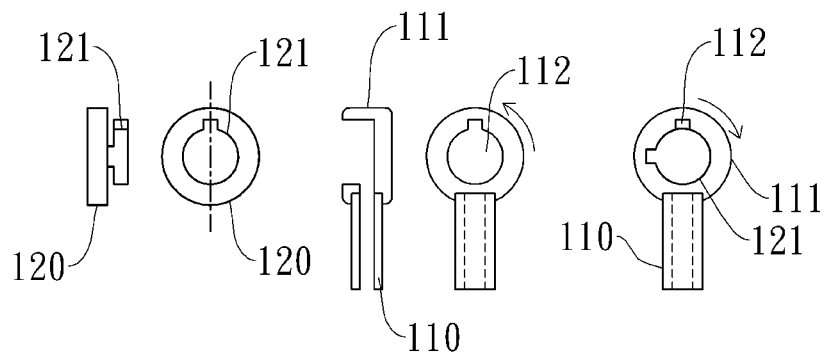

The tooth pairing part 120 and the pairing structure 121 of the conduit pairing part 111 can be of any shapes that are complementary to each other. As shown in FIG. 1B in the present embodiment, the pairing structure 121 is a disk-like fastening structure and the conduit paring part 111 has a cylindrical space 112 that is complementary to the pairing structure 121. After the paring structure 121 is fitted into the matching space 112, the conduit pairing part 111 can be rotated to interlock itself with the tooth paring part 120. Once the tooth paring part 120 and conduit pairing part 111 are physically connected, a negative pressure source 100 can draw air out of oral cavity and thus produce a negative pressure environment to pull the tongue, soft palate and other soft tissue forward to maintain the airway patency.

Figure 1C:
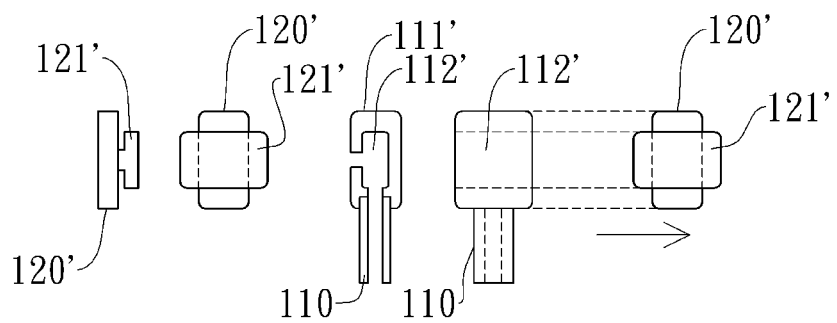
FIG. 1C shows a variation of the first embodiment of the present invention.

FIG. 1C is a variation of the present embodiment with a tooth pairing part and a conduit pairing part. The pairing structure 121' of the tooth pairing part 120' is a rail-like fastening structure and the conduit paring part 111' has a slot-like space 112's that is complementary to the pairing structure 121'. Once the pairing structure 121' is slid into the matching space 112', a negative pressure source 100 can draw air out of oral cavity and thus produce a negative pressure environment to pull the tongue, soft palate and other soft tissue forward to maintain the airway patency.

Figure 2A:
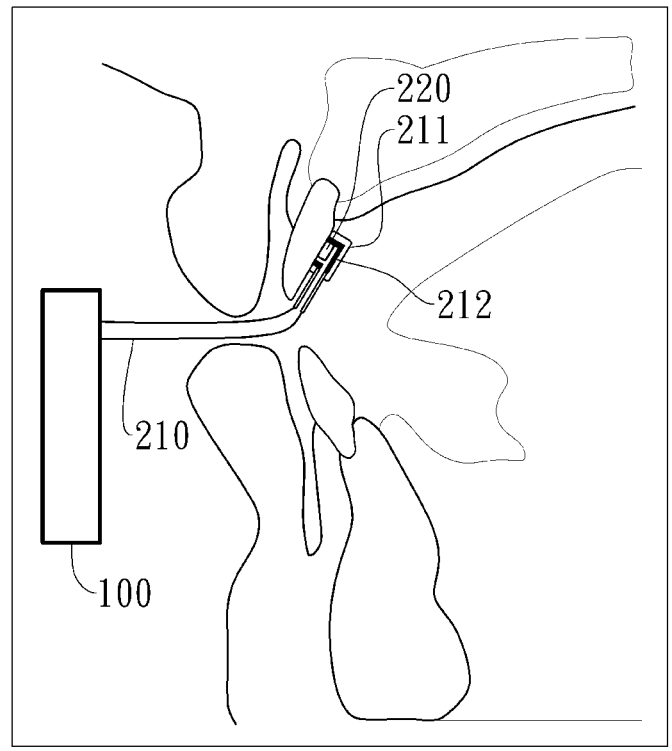
FIG. 2A and FIG. 2B show schematic diagrams of an oral apparatus according to the second embodiment of the present invention.

FIG. 2A is a cross-section view of a negative pressure oral apparatus according to a second embodiment of the present invention. The negative pressure oral apparatus comprises a fluid conduit 210, a fixation part which is a tooth pairing part 220, and a conduit pairing part 211 near the end of the fluid conduit 210. The tooth paring part 220 can be attached to the surface of teeth by gluing or bonding permanently or temporarily. The tooth pairing part 220 may be a magnetic or paramagnetic part. The conduit pairing part 211 has a pairing structure 212 which can magnetically attach to the tooth paring part 220. Once the tooth paring part 220 and conduit pairing part 211 are physically connected, a negative pressure source 100 can draw air out of oral cavity and thus produce a negative pressure environment to pull the tongue, soft palate and other soft tissue forward to maintain the airway patency.

Figure 2B:
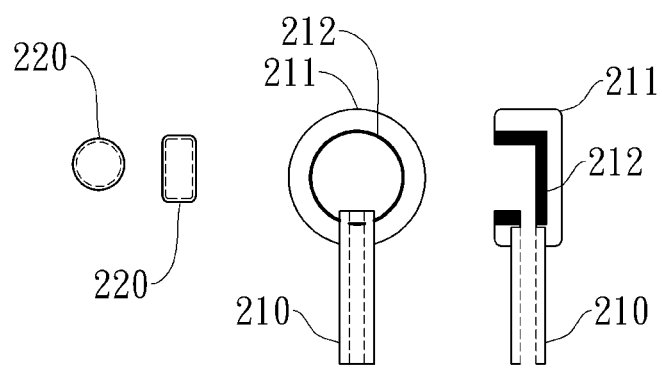

As shown in FIG. 2B, the pairing structure 212 is a disk-like paramagnetic or magnetic part with a cylindrical space that is complementary to the tooth pairing part 220. The tooth pairing part 220 and the pairing structure 212 can be of any shapes that are complementary to each other. After the tooth pairing part 220 is magnetically attached to the pairing structure 212, a negative pressure source 100 can draw air out of oral cavity and thus produce a negative pressure environment to pull the tongue, soft palate and other soft tissue forward to maintain the airway patency.

Figure 3A:
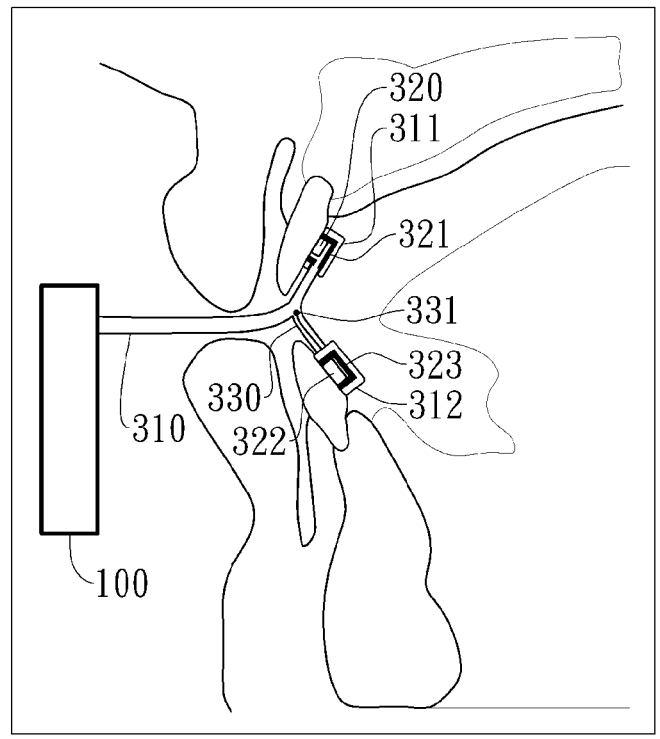
FIG. 3A to FIG. 3C show schematic diagrams of an oral apparatus according to the third embodiment of the present invention.
Figure 3B:
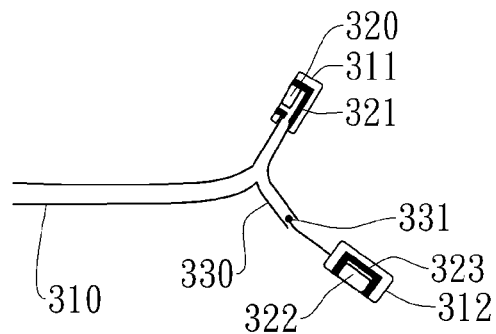
Figure 3C:
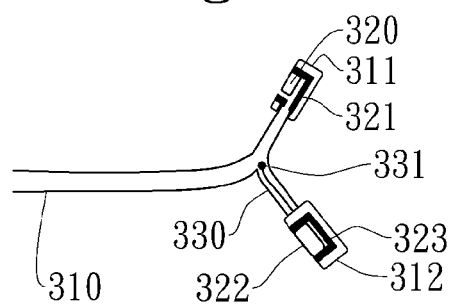

FIG. 3A is a cross-section view of a negative pressure oral apparatus according to a third embodiment of the present invention. The negative pressure oral apparatus comprises a fluid conduit 310, a first fixation part which is a first tooth pairing part 320, and a first conduit pairing part 311 near the end of the fluid conduit 310. The negative pressure oral apparatus also has a second fixation part which is a second tooth pairing part 322 and a second conduit pairing part 312 near the end of the fluid conduit 310 opposite to the first conduit pairing part 311. The first and second tooth paring parts, 320 and 322, can be attached to the surface of upper or lower teeth by gluing or bonding permanently or temporarily. The first and second tooth pairing parts, 320 and 322, can be mechanically and magnetically connected and disconnected with the first and second conduit paring parts, 311 and 312. The first and second tooth pairing parts, 320 and 322, can prevent the present negative pressure oral apparatus from falling off from the user's mouth and can also prevent the mouth from opening. A negative pressure source 100 can draw air out of oral cavity and thus produce a negative pressure environment to pull the tongue, soft palate and other soft tissue forward to maintain the airway patency. One of conduit pairing parts, 311 or 312, may further have a piston end 331 which inserts into a cylinder end 330 of the conduit 310. FIG. 3B shows the piston end 331 in an expanded state without negative pressure applied, whereas the mouth is allowed to open. FIG. 3C shows the piston end 331 in a retracted state with negative pressure applied, whereas the maxilla and mandible are holding closely to prevent mouth from opening. The retracting force generated by negative pressure applied to the cylinder end 330 and the piston end 331 may be adjustable and enough to close the mouth when muscle is relaxed and patient may still open the mouth if he/she intends to do so when the negative pressure is applied.

Figure 4A:
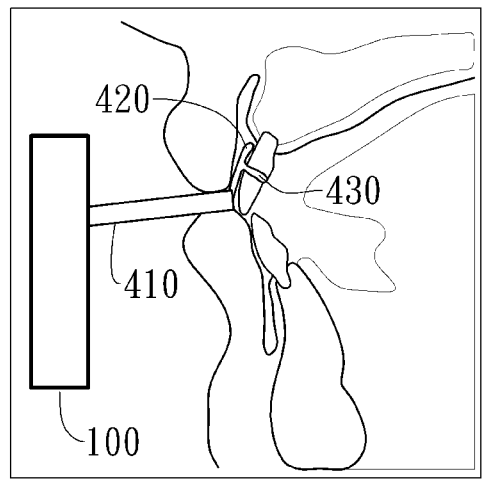
FIG. 4A to FIG. 4C show schematic diagrams of an oral apparatus according to the fourth embodiment of the present invention.

FIG. 4A is a side cross-section view of a negative pressure oral apparatus according to a fourth embodiment of the present invention. The negative pressure oral apparatus comprises a fluid conduit 410 and a fixation part which further comprises a slit fastening part 430 and a plate 420. The first opening of the fluid conduit 410 is connected to one face of the plate 420. The slit fastening part 430 extends from one end of the plate 420 to the other end of the plate 420. The slit fastening part 430 can be inserted into the slit(s) between teeth and the plate 420 can be held by the slit fastening part 430 against the surface of teeth. The slit fastening part 430 and/or the plate 420 may have an elastic property that can hold the fluid conduit 410 in place. A negative pressure source 100 connected to the air conduit 410 can draw air out of oral cavity and thus produce a negative pressure environment to pull the tongue, soft palate and other soft tissue forward to maintain the airway patency.

Figure 4B:
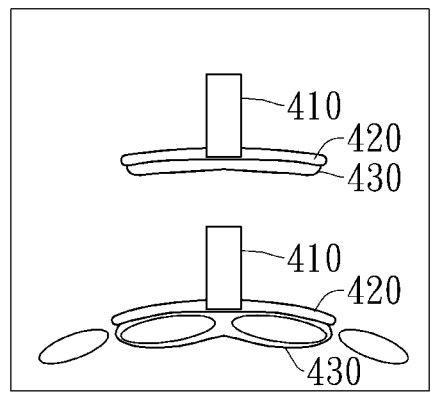
Figure 4C:
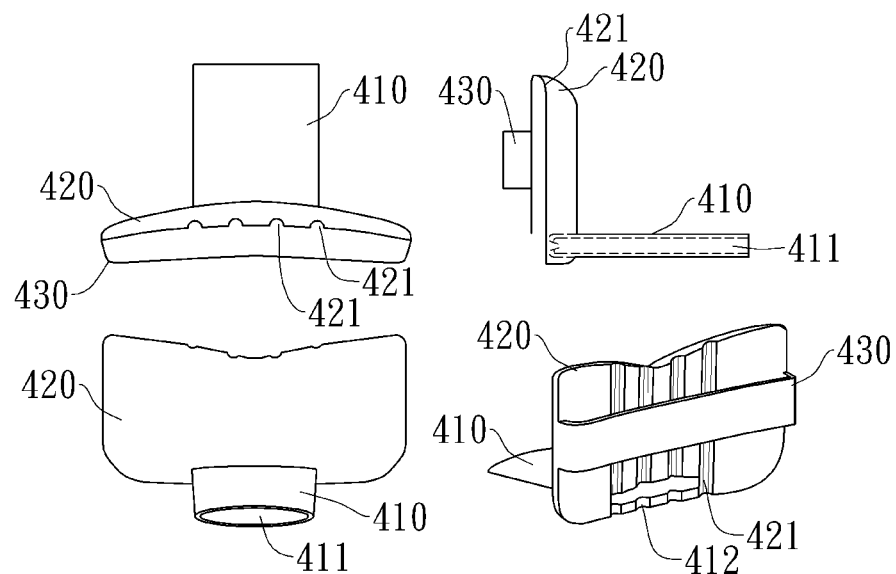

FIG. 4B shows a top cross-section view of the negative pressure oral apparatus according to a fourth embodiment of the present invention. The plate 420 may cover at least width of one tooth and preferably width of two teeth. The slit fastening part 430 may be stemmed from one end of the plate 420 to the other end of the plate 420. The slit fastening part 430 can be stretched and inserted in to the slits of teeth. The recoiling force can pull the plate 420 against one side of the teeth and the slit fastening part 430 against the other side of the teeth thus prevent the fluid conduit 410 from falling off. FIG. 4C shows different views of the 3D drawings of a negative pressure oral apparatus according to a fourth embodiment. The fluid conduit 410 has a channel 411 with an opening on the plate 420 and the fluid conduit 410. The plate 420 may have one or more grooves 421 on the surface facing the teeth that will help distribute the negative pressure. The slit fastening part 430 can be a strap or be composed of multiple wires to provide enough strength and coverage to hold the teeth.

Figure 4D:
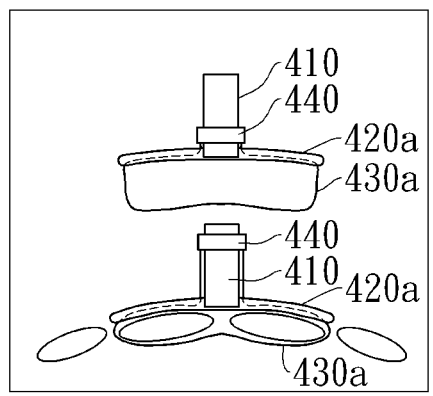
FIG. 4D to FIG. 4G show variations of the first embodiment of the present invention.

FIG. 4D shows a top cross-section view of a variation of the fourth embodiment of the present invention. The plate 420a may cover at least width of one tooth and preferably width of two teeth. The slit fastening part 430a may be a floss-like wire from one end of the plate 420a to the other end of the plate 420a. The slit fastening part 430a with extra length passes through the plate 420a and is connected to a sliding part 440 on the first opening of the fluid conduit 410. The slit fastening part 430a can be inserted in to the slits of teeth. Then the slit fastening part 430a can be pulled by moving the sliding part from the other side of the plate 420a and applies or adjusts contraction force on the teeth thus prevent the fluid conduit 410 from falling off. The slit fastening part 430a can be fixed by the friction force on the contact surface between the plate 420a and the slit fastening part 430a, or it can be fixed by the friction force between the sliding part 440 and the fluid conduit 410.

Figure 4E:
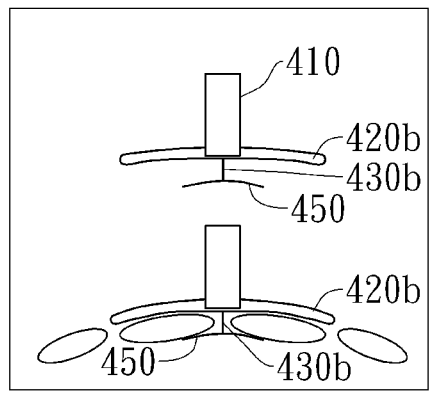

FIG. 4E shows a top cross-section view of yet another variation of the fourth embodiment of the present invention. The plate 420b may cover at least both halves of two teeth and preferably the total width of two teeth. The slit fastening part 430b may be a flexible T-shape stemmed preferably from the center of the plate 420b. The slit fastening part 430b can be stretched and inserted in to the slits of teeth. The slit fastening part 430b can further have an extending plate 450 which will apply contraction force on the teeth when the slit fastening part 430b recoil after being stretched thus prevent the fluid conduit 410 from falling off. The negative pressure oral apparatus may have multiple slit fastening parts 430b and extending plates 450 to provide more strength and coverage to hold teeth.

Figure 4F:
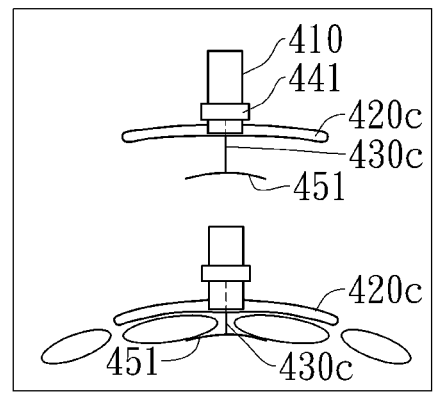

FIG. 4F shows a top cross-section view of still another variation of the fourth embodiment of the present invention. The plate 420c may cover at least both halves of two teeth and preferably the total width of two teeth. The slit fastening part 430c may be a floss-like wire ended at an extending plate 451 and preferably being connected to the center of the plate 420c. The slit fastening part 430c may have extra length and pass through the plate 420c and is connected to a sliding part 441. The slit fastening part 430c can be inserted in to the slits of teeth. Then the slit fastening part 430c can be pulled by moving the sliding part 441 from the other side of the plate 420c and applies or adjusts contraction force on the teeth with an extending plate 451, thus prevent the fluid conduit 410 from falling off. The slit fastening part 430c can be fixed by the friction force on the contact surface between the plate 420c and the slit fastening part 430c, or it can be fixed by friction force between the sliding part 441 and the fluid conduit 410.

Figure 4G:
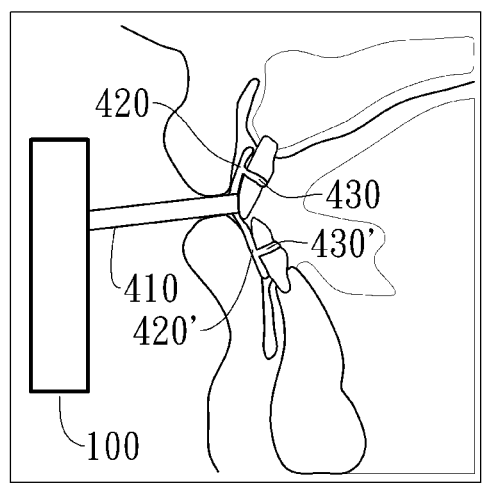

FIG. 4G is a still another variation of the fourth embodiment of the present invention. The negative pressure oral apparatus comprises a fluid conduit 410 and a first fixation part which further comprises a plate 420 and a first slit fastening part 430. The negative pressure oral apparatus may further have a second fixation part which comprises a extending second plate 420' and a second slit fastening part 430'. The first slit fastening part 430 can be inserted into the slit(s) of upper teeth and the first plate 420 can rest against the surface of upper teeth. The first slit fastening part 430 and/or the first plate 420 may have an elastic property that can hold the fluid conduit 410 in place. The second slit fastening part 430' can be inserted into the slit(s) of lower teeth and the extending second plate 420' can rest against the surface of lower teeth. The second slit fastening part 430' and/or the extending second plate 420' may have an elastic property that can hold the fluid conduit 410 in place. A negative pressure source 100 connected to the air conduit 410 can draw air out of oral cavity and thus produce a negative pressure environment to pull the tongue, soft palate and other soft tissue forward to maintain the airway patency.

Figure 5A:
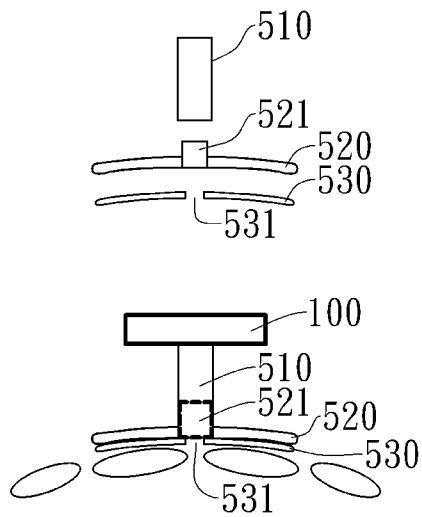
FIG. 5A to FIG. 5C show schematic diagrams of an oral apparatus and a variation according to the fifth embodiment of the present invention.
Figure 5B:
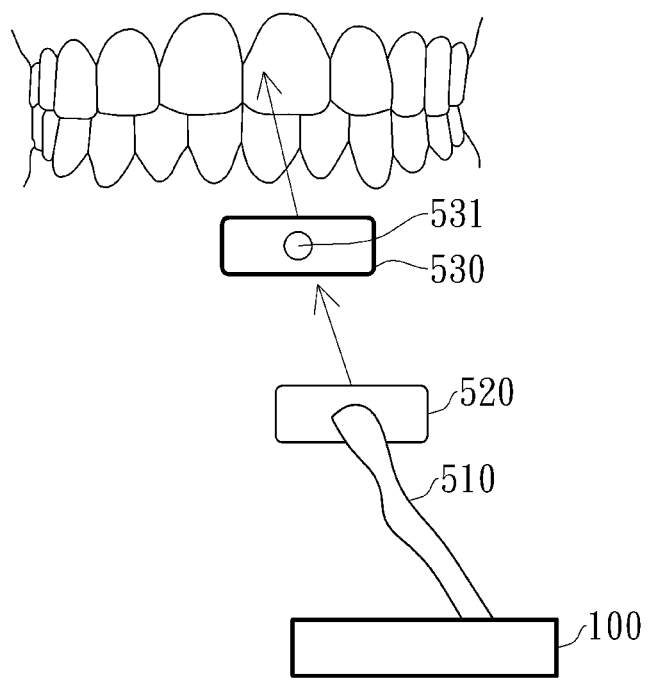

FIG. 5A shows the top view and FIG. 5B shows the front view of a negative pressure oral apparatus according to the fifth embodiment of the present invention. The negative pressure oral apparatus comprises a fluid conduit 510 and a fixation part which further comprises a conduit-attachment plate 520 and an adhesive film 530. The conduit-attachment plate 520 has an opening connected to the first opening of the fluid conduit 510, and one surface of the adhesive film 530 adheres to one surface of the conduit-attachment plate 520. The conduit-attachment plate 520 may further have a conduit interface 521 to allow the fluid conduit 510 and the attachment plate 520 to be separable therefore allowing easier cleaning or replacement. The adhesive film 530 can be a double-sided, disposable adhesive membrane or multiple-use adhesive layer that may have peel-off backings. The adhesive film 530 can also be materials (such as edible glue, temporary glue, chewing gum, clay, gel, foam) which can be applied to the surface of oral interface and/or the teeth. The length and width of the adhesive film 530 may be about the size of the attachment plate 520, preferably 2~4 teeth-wide and the one-tooth height. One side of the adhesive film 530 is adhered to the teeth, and the other side of the membrane is adhered to the attachment plate 520. The adhesive film 530 may have an opening 531, which is to be aligned with fluid conduit 510 to allow air flow. Once the adhesive film 530 is attached to the attachment plate 520 on one side and attached to the teeth on the other side, a negative pressure source 100 can draw air out of oral cavity and thus produce a negative pressure environment to pull the tongue, soft palate and other soft tissue forward to maintain the airway patency.

As shown in FIG. 5B, the fluid conduit 510 and attachment plate 520 can be a one-piece design without the conduit interface 521.

Figure 5C:
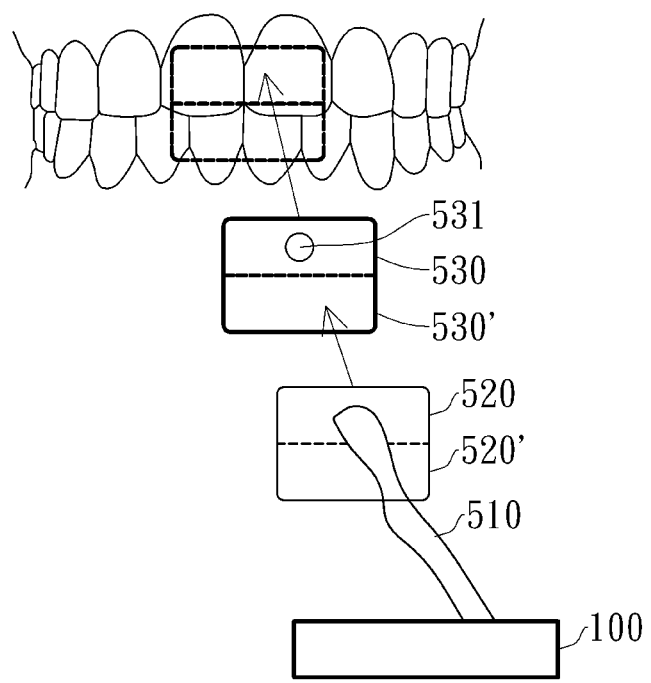

FIG. 5C shows a variation of the fifth embodiment of the present invention. The negative pressure oral apparatus comprises a fluid conduit 510 and a first fixation part which further comprises a conduit-attachment plate 520 and a first adhesive film 530, and a second fixation part which further comprises an extending plate 520' and a second adhesive film 530'. The first adhesive film 530 may have an opening 531, which is to be connected with fluid conduit 510 to allow air flow. The first adhesive films 530 is attached to the attachment plate 520 on one side and attached to the upper teeth on the other side. The second adhesive films 530' is attached to the attachment plate 520 on one side and attached to the lower teeth on the other side. A negative pressure source 100 can be connected to a second opening of the fluid conduit 510.

Figure 6A:
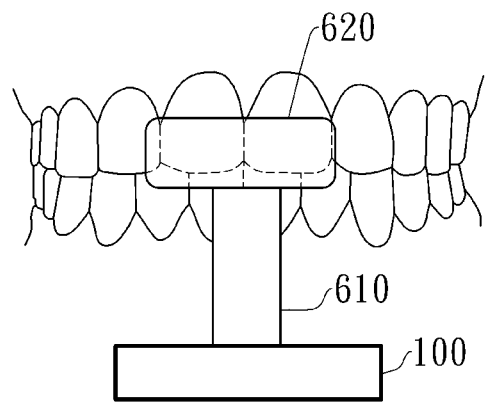
FIG. 6A and FIG. 6B show schematic diagrams of an oral apparatus according to the sixth embodiment of the present invention.
Figure 6B:
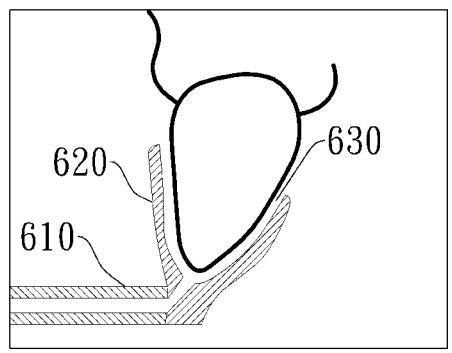

FIG. 6A represents the front view and FIG. 6B represents the cross-section view of a negative pressure oral apparatus according to the sixth embodiment of the present invention. The negative pressure oral apparatus comprises a fluid conduit 610, and fixation part which is a tooth sheath 620. The tooth sheath 620 can be made of silicone or other soft material to directly deliver negative pressure to the teeth. As shown in FIG. 6B, the tooth sheath 620 wraps around the teeth and may have one or more pores 621 connected to the fluid conduit 610. The inner surface of the tooth sheath may have multiple grooves 630, serving as air channel to not only deliver negative pressure to the teeth but also deliver negative pressure to the oral cavity.

Figure 6C:
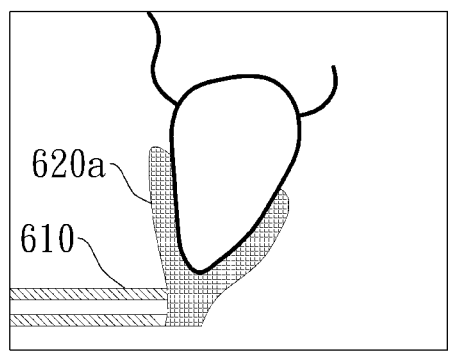
FIG. 6C shows a variation of the sixth embodiment of the present invention.

FIG. 6C represents the front view of a variation according to the sixth embodiment of the present invention. The tooth sheath 620a is made of porous material that can still deliver negative pressure while collapsed. The tooth sheath 620a can serve as air channels to not only deliver negative pressure to the teeth but also deliver negative pressure to the oral cavity. Once the teeth sheath 620a is applied and covers the teeth, a negative pressure source 100 can draw air out of oral cavity, allowing the teeth attachment 620a to remain fixed to the teeth, and producing a negative pressure environment to pull the tongue, soft palate and other soft tissue forward to maintain the airway patency.

Figure 7A:
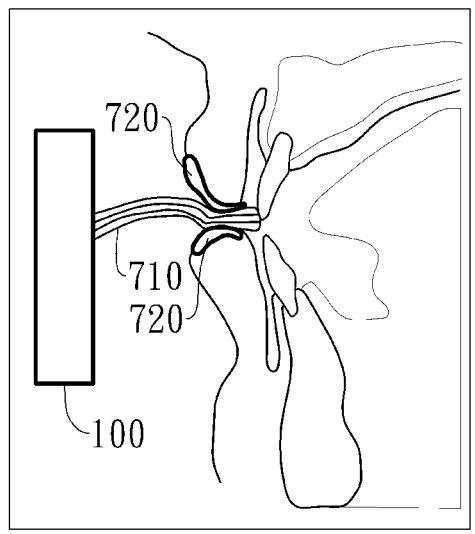
FIG. 7A and FIG. 7B show schematic diagrams of an oral apparatus according to the seventh embodiment of the present invention.
Figure 7B:
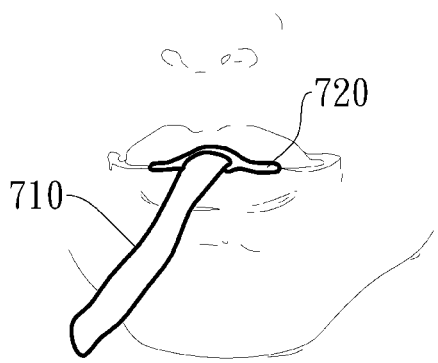

FIG. 7A represents the cross-section view and FIG. 7B represents the front view of a negative pressure oral apparatus according to the seventh embodiment of the present invention. The negative pressure oral apparatus comprises of a fluid conduit 710, and a fixation part which is an adhesive layer 720. The adhesive layer 720 is applied to the region around upper and lower lips to secure the fluid conduit 710 and prevent the mouth from opening. The adhesive layer 720 may also fill any space between the lip and the fluid conduit 710, therefore preventing air leakage, as shown in FIG. 7B. The adhesive layer 720 may only be applied to lip region around the fluid conduit 710, and it will not totally occluded the opening of the mouth. The partial application of the adhesive layer 720 allows the user to exhale air through the mouth if needed. The materials of the adhesive layer 720 may include, but not limited to, grease (such as petrolatum), glue (edible and washable), oral cream or oral gel. Once the fluid conduit 710 is secured in the mouth with the adhesive layer 720, a negative pressure source 100 can draw air out of oral cavity and thus produce a negative pressure environment to pull the tongue, soft palate and other soft tissue forward to maintain the airway patency.

Figure 7C:
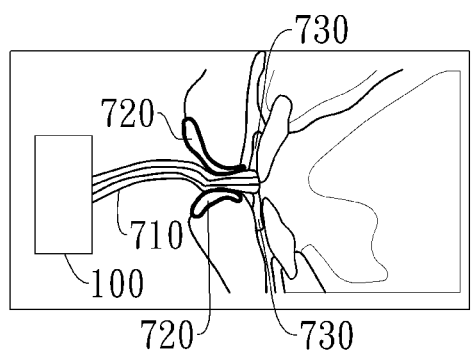
FIG. 7C shows a variation of the seventh embodiment of the present invention.

FIG. 7C represents the cross-section view of a variation of the seventh embodiment. A securing plate 730 extended from the end of the fluid conduit 710 can be inserted between lips and teeth. The securing plate 730 can further help secure the fluid conduit 710 in the mouth.

Figure 8A:
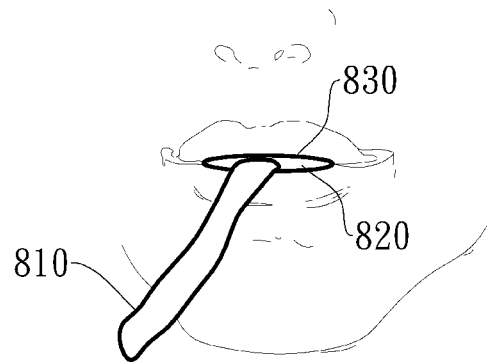
FIG. 8A to FIG. 8C show schematic diagrams of an oral apparatus according to the eighth embodiment of the present invention.
Figure 8B:
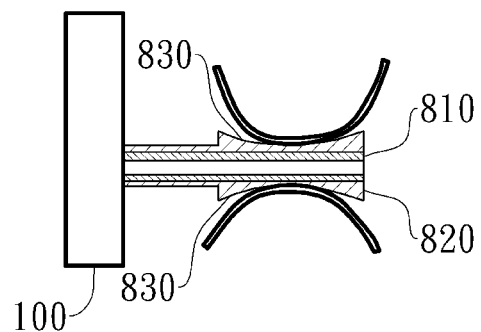
Figure 8C:
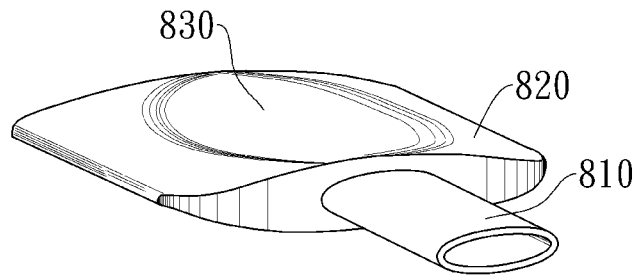
Figure 8D:
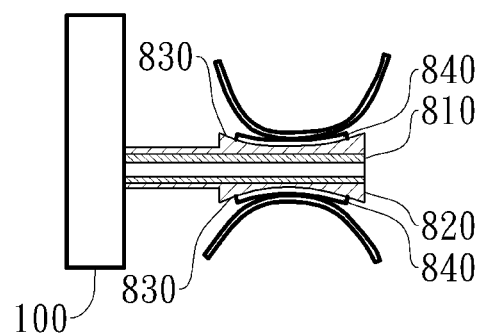
FIG. 8D shows a variation of the eighth embodiment of the present invention.

FIG. 8A represents the front view and FIG. 8B represents the cross view of a negative pressure oral apparatus according to the eighth embodiment of the present invention. FIG. 8C is the 3D view of the negative pressure oral apparatus. The negative pressure oral apparatus comprises of a fluid conduit 810, a fixation part which is a lip interface 820 and a contoured surface 830. The contoured surface 830 is conformal to the shape of the opening of month. As shown by the cross-section view of the oral apparatus in FIG. 8B, the contoured surface 830 of the lip interface 820 is also curved and raised at both ends to match the cross-sectional surface of the lips. The contoured surface 830 may be made of a self-adhesive material, such as silicone rubber, to help secure the fluid conduit 810. An adhesive layer 840 may be applied onto the contoured surface 830 to increase the securing force, as shown in FIG. 8D. The materials of the adhesive layer 840 may include, but not limited to, grease (such as petrolatum), glue (edible and washable), oral cream, oral gel, or double-sided tape. The adhesive layer 840 may only be applied to lip region around the contoured surface 830 without totally occluding the opening of the mouth. Partial application of the adhesive layer 840 allows the user to exhale air through the mouth if needed.

The oral interface 820 can also be made of flexible material to fit comfortably between lips. The secure fitting of the oral interface 820 to the lip maintains closing of the mouth while negative pressure is being delivered. Once the fluid conduit 810 is secured in the mouth via the oral interface 820, a negative pressure source 100 can draw air out of oral cavity and thus produce a negative pressure environment to pull the tongue, soft palate and other soft tissue forward to maintain the airway patency.

Figure 9A:
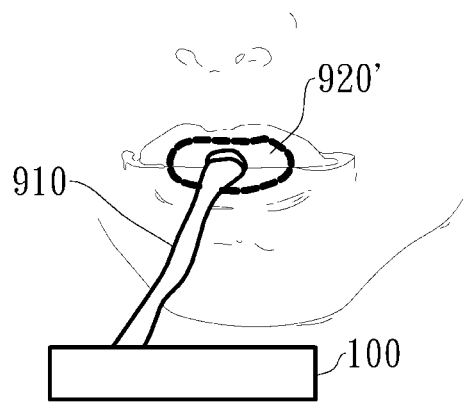
FIG. 9A show a schematic diagram of an oral apparatus according to the ninth embodiment of the present invention.

FIG. 9A represents the front view of a negative pressure oral apparatus according to the ninth embodiment of the present invention. The negative pressure oral apparatus comprises of a fluid conduit 910, and a fixation part which is an adhesive part or tape 920. The adhesive part 920 can be temporarily attached to the skin as well as to the fluid conduit and is used to secure the fluid conduit and to keep the mouth closed. The adhesive part 920 may only be applied to lip region around the fluid conduit 910 without totally occluding the opening of the mouth. The sealing of the mouth will be reached by the lips itself at lip region where the adhesive part 920 is not covered. Once the tape and the fluid conduit are physically connected, a negative pressure source 100 can draw air out of oral cavity and thus produce a negative pressure environment to pull the tongue, soft palate and other soft tissue forward to maintain the airway patency.

Figure 9B:
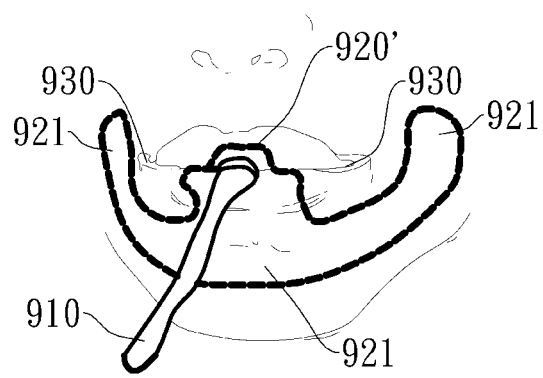
FIG. 9B to FIG. 9E show variations of the ninth embodiment of the present invention.
Figure 9C:
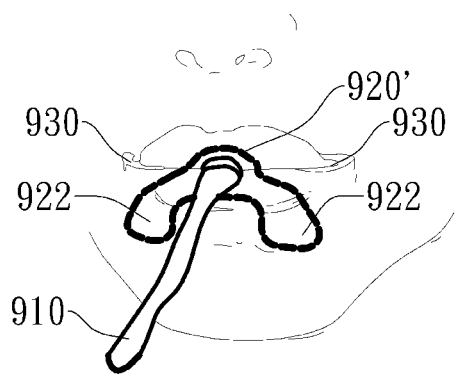
Figure 9D:
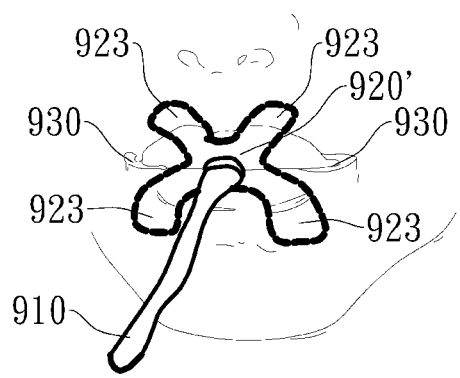

FIGS. 9B, 9C and 9D represent the variations of the negative pressure oral apparatus according to the ninth embodiment of the present invention. The negative pressure oral apparatus comprises of a fluid conduit 910 and a first fixation part which is an adhesive part or tape 920', and it further comprises a second fixation part which is an extending adhesive part 921, 922, or 923. The adhesive part 920' and the extending adhesive part 921, 922 or 923 can be designed to have various shapes to increase the holding force to prevent the mouth from opening, and may have one to several partial opening(s) 930 to preserve the mouth opening regions not completely covered by the adhesive parts.

Figure 9E:
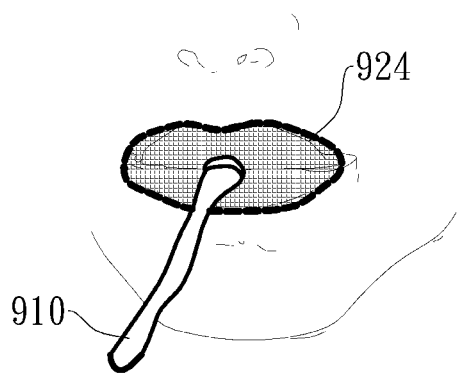

FIG. 9E represents the front view of yet another negative pressure oral apparatus according to the ninth embodiment of the present invention. The adhesive part 924 may be a breathable tape with arrays of venting holes that covers the opening area of the mouth. The venting holes of adhesive part 924 and the partial opening 930 of the adhesive parts 920', 921, 922, and 923 allow the user to exhale air through the mouth if needed.

Figure 10A:
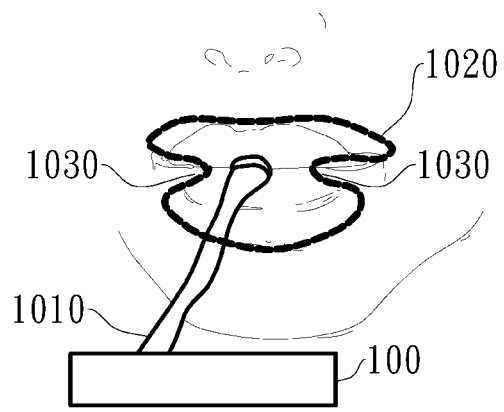
FIG. 10A shows a schematic diagram of an oral apparatus according to the tenth embodiment of the present invention.

FIG. 10A represents the front view of a negative pressure oral apparatus according to the tenth embodiment of the present invention. The negative pressure oral apparatus comprises of a fluid conduit 1010, and a fixation part which is a cosmetic mask 1020. The fluid conduit 1010 has a first opening which is connected to the cosmetic mask 1020 and extends into the user's oral cavity. The fluid conduit has a second opening which can be connected to a negative pressure source 100. The cosmetic mask 1020 can be temporarily attached to the skin and to the fluid conduit 1010, and is used to secure the fluid conduit 1010 and to keep the mouth closed. The mask can be liquid, cream, paper or cloth based for easy application. Once the cosmetic mask 1020 and the fluid conduit 1010 are physically connected, the negative pressure source 100 can draw air out of oral cavity and thus produce a negative pressure environment to pull the tongue, soft palate and other soft tissue forward to maintain the airway patency. As shown in FIG. 10A the cosmetic mask 1020 in the present embodiment can be designed with various shapes to increase the holding force and prevent the mouth from opening. The cosmetic mask 1020 may have partial openings 1030 to preserve the lip regions where the opening of the mouth will not be occluded entirely by the cosmetic mask 1020.

Figure 10B:
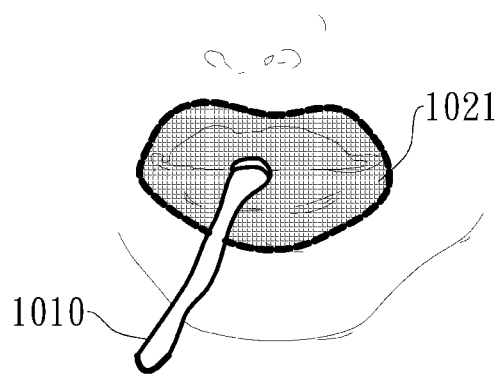
FIG. 10B shows a variation of the tenth embodiment of the present invention.

FIG. 10B represents the front view of a variation of the tenth embodiment of the present invention. The cosmetic mask 1021 may be a breathable mask with arrays of venting holes that covers the opening area of the mouth. The venting holes of the cosmetic mask 1021 and the partial opening 1030 of the cosmetic mask 1020 allow the user to exhale air through the mouth if needed.

Figure 11A:
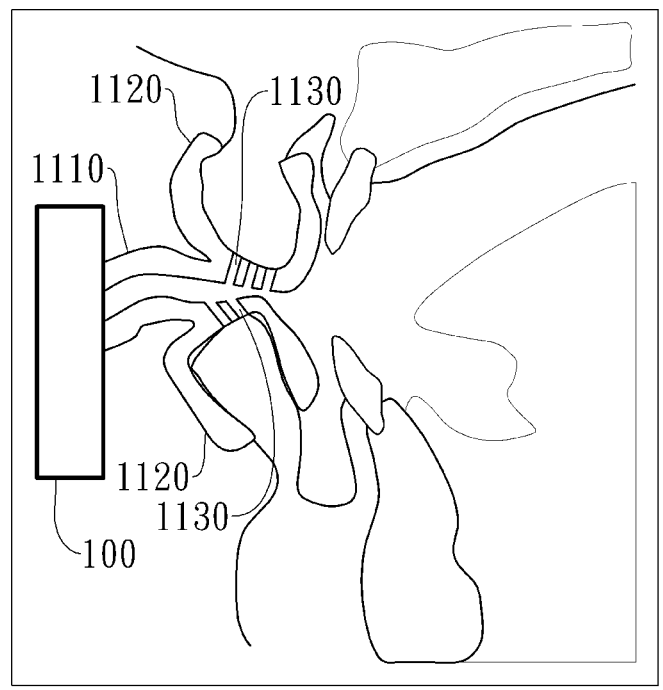
FIG. 11A and FIG. 11B show schematic diagrams of an oral apparatus according to the eleventh embodiment of the present invention.

FIG. 11A shows a cross sectional view of a negative pressure oral apparatus according to the eleventh embodiment of the present invention. The negative pressure oral apparatus comprises of a fluid conduit 1110, and a fixation part which is a lip interface 1120 to be fitted on user's lips. The fluid conduit 1110 has a first opening connected to the lip interface 1120 and extends into the user's oral cavity. The fluid conduit 1110 also has a second opening which can be connected to a negative pressure source 100. The lip interface 1120 contains multiple pores 1130 connecting first opening of the fluid conduit 1110 with the upper and lower lips which allow negative pressure from the source 100 to pull the interface towards the lips, secure the position of the fluid conduit 1110 and keep the mouth closed. The negative pressure source 100 can then draw air out of the oral cavity and thus produce a negative pressure environment to pull the tongue, soft palate and other soft tissue forward to maintain the airway patency.

Figure 11B:
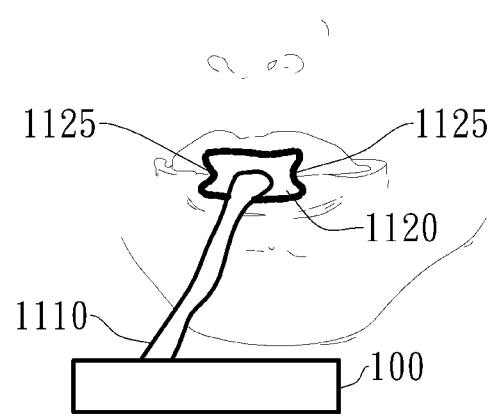

As shown in FIG. 11B the lip interface 1120 may have partial openings 1125 to preserve the lip regions where the opening of the mouth will not be occluded entirely by the lip interface 1120. The partial opening 1030 of lip interface 1120 allows the user to exhale air through the mouth if needed.

FIG. 12A shows a cross sectional view of a negative pressure oral apparatus according to the twelfth embodiment of the present invention. The negative pressure oral apparatus comprises of a fluid conduit 1210, and a fixation part which is a porous interface 1230 extending into the oral cavity. The air conduit 1210 has a first opening connected to the porous interface 1230. The air conduit 1210 also has a second opening which can be connected to a negative pressure source 100. The porous interface 1230 is made out of porous material which has a property that allows negative pressure from the source 100 to draw air out of the oral cavity and thus produce a negative pressure environment to pull the tongue, soft palate and other soft tissue forward to maintain the airway patency. When negative pressure is applied, the porous interface 1230 will be compressed and deformed its shape compliant to the internal shape of the oral cavity while it still preserves its ability to delivery negative pressure to the oral cavity.

FIG. 12B shows the cross view of a variation of the twelfth embodiment of the present invention. The negative pressure oral apparatus further comprises a second fixation part which is an external shield 1220 connected to the fluid conduit 1210. The external shield 1220 is situated outside the mouth to prevent the user from swallowing the apparatus and secure the position of the porous interface 1230 within the oral cavity. The external shield 1220 may be attached to the skin near upper and lower lips to keep the user's mouth closed. The external shield 1220 does not cover the entire mouth opening.

FIG. 12C shows another variation of the twelfth embodiment of the present invention. The negative pressure oral apparatus further comprises a second fixation part which is an internal shield 1240 connected to the fluid conduit 1210. The internal shield 1240 is situated inside the oral cavity between lips and teeth to secure the position of the porous interface 1230 within the oral cavity and to prevent the user from swallowing the apparatus. The internal shield 1240 does not cover the entire region of mouth opening and may be attached to the upper and lower lips or teeth to keep the user's mouth closed.

Figure 12D:
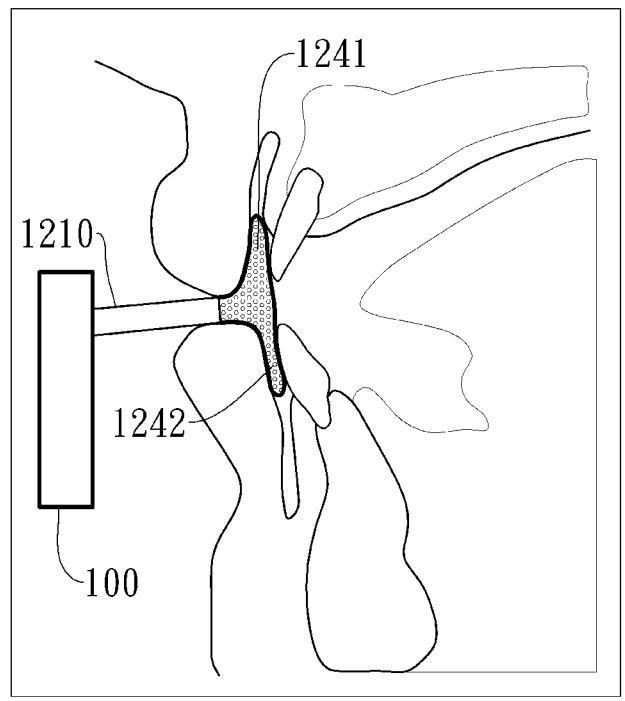

FIG. 12D shows yet another variation of the twelfth embodiment of the present invention. The negative pressure oral apparatus comprises a first fixation part which is a shielding porous interface 1241 connected to the fluid conduit 1210. The shielding porous interface 1241 is situated inside the oral cavity between upper lip and upper teeth to secure its position within the oral cavity and to prevent the user from swallowing the apparatus. The negative pressure oral apparatus may further comprise a second fixation part which is an extending porous part 1242. The extending porous part 1242 extends from the shielding porous interface 1241 into the space between lower lip and lower teeth. The shielding porous interface 1241 and the extending porous part 1242 are made of porous material that has a property that allows negative pressure from the source 100 to draw air out of the oral cavity and thus produce a negative pressure environment to pull the tongue, soft palate and other soft tissue forward to maintain the airway patency. When negative pressure is applied, the shielding porous interface 1241 and the extending porous part 1242 will be compressed and deformed its shape compliant to the internal shape of the oral cavity while it still preserves its ability to delivery negative pressure to the oral cavity.

Figure 12E:
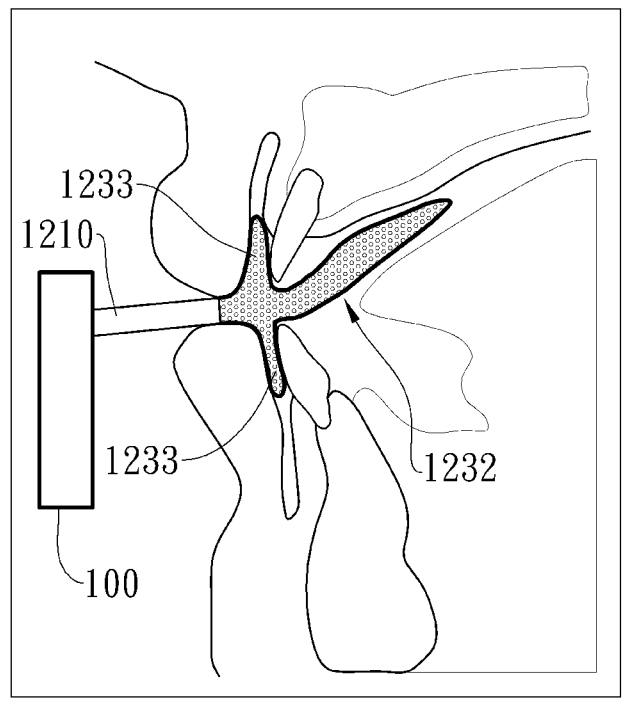

FIG. 12E shows still another variation of the twelfth embodiment of the present invention. The negative pressure oral apparatus comprises of a fluid conduit 1210 and a first fixation part which is a porous interface 1232 extending into the oral cavity. The porous interface 1232 has a second fixation part which is upper and lower shielding extensions 1233 situated between lips and teeth to keep the user's mouth closed and secure oral apparatus's position within the oral cavity and to prevent the user from swallowing the apparatus. The porous interface 1232 and the shielding extensions 1233 are made out of porous material which has a property that allows negative pressure from the source 100 to draw air out of the oral cavity and thus produce a negative pressure environment to pull the tongue, soft palate and other soft tissue forward to maintain the airway patency. When negative pressure is applied, the porous interface 1232 and the shielding extensions 1233 will be compressed and deformed their shape compliant to the internal shape of the oral cavity while they still preserve their ability to delivery negative pressure to the oral cavity.

Figure 13A:
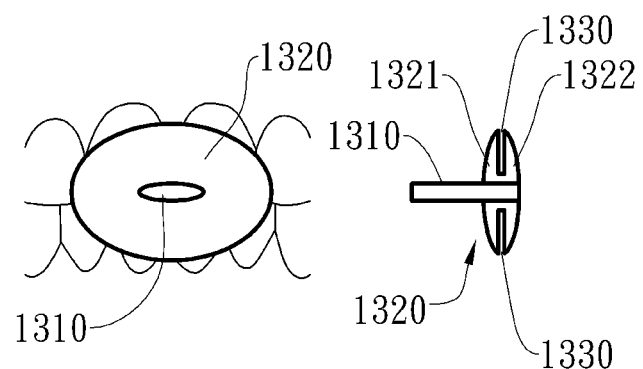
FIG. 13A to FIG. 13B show schematic diagrams of an oral apparatus according to the thirteenth embodiment of the present invention.
Figure 13B:
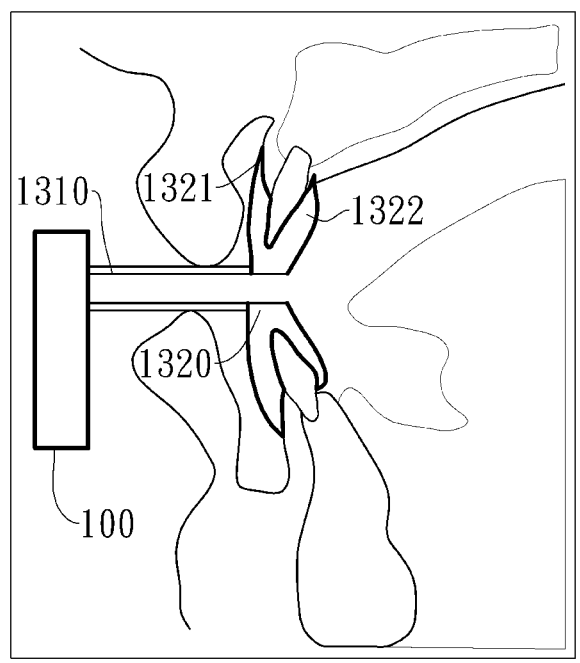

FIG. 13A shows front and side views of a negative pressure oral apparatus according to the thirteenth embodiment of the present invention. The negative pressure oral apparatus comprises of a fluid conduit 1310, and a fixation part which is a tooth clip 1320. The air conduit 1310 has a first opening connected to the tooth clip 1320 and extends into the user's oral cavity. The air conduit 1310 also has a second opening which can be connected to a negative pressure source 100. The tooth clip 1320 consists of a front part 1321, a back part 1322, and a slit 1330 in between. As shown in FIG. 13B, the fluid conduit 1310 goes through the tooth clip 1320 to the oral cavity. The teeth clip 1320, the front part 1321 and the back part 1322 can clip onto both upper and lower teeth tightly. The negative pressure source 100 can draw air out of the oral cavity and thus create a negative pressure environment to pull the tongue, soft palate and other soft tissue forward to maintain the airway patency. The tooth clip 1320, the front part 1321, and the back part 1322 can be made of elastic material as an integral part. As shown in FIG. 13A, the tooth clip 1320 may be a few tooth-wide. For patients' comfort, the front part 1321 and the back part 1322 may not be long enough to contact the gum.

Figure 14A:
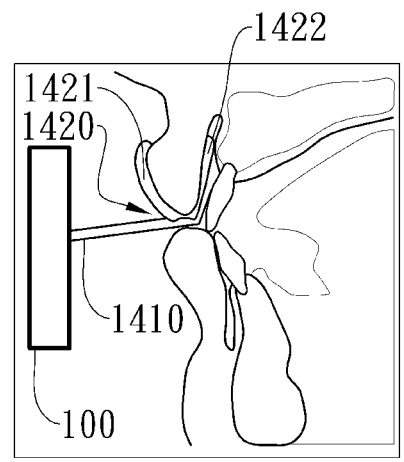
FIG. 14A to FIG. 14C show schematic diagrams of an oral apparatus according to the fourteenth embodiment of the present invention.
Figure 14B:
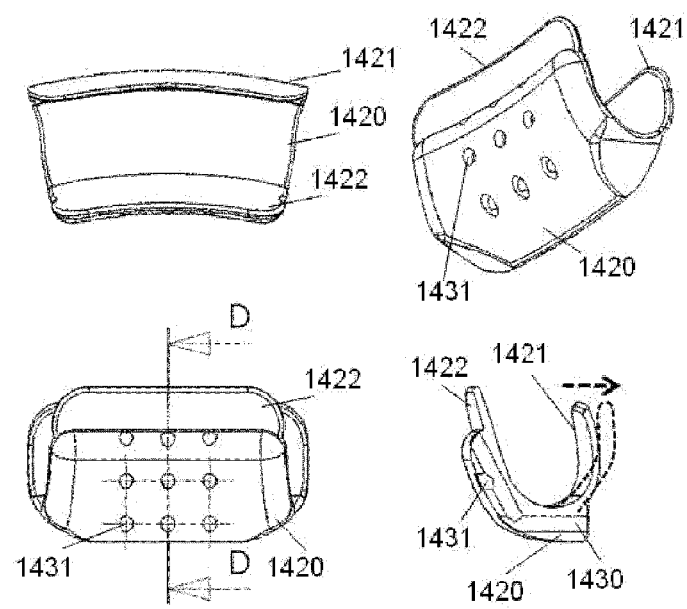
Figure 14C:
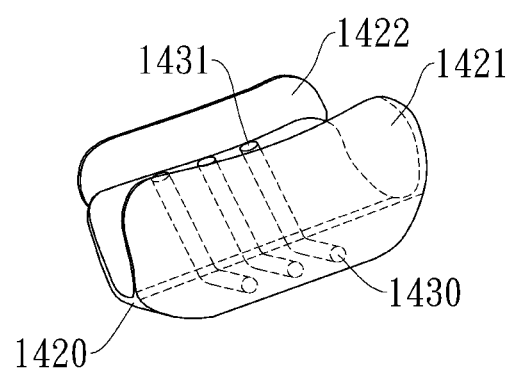

FIG. 14A represents a cross-section view and FIG. 14B to FIG. 14C represent different 3D views of a negative pressure oral apparatus according to the fourteenth embodiment of the present invention. The negative pressure oral apparatus comprises of a fluid conduit 1410, a fixation part which is a lip interface 1420. The lip interface 1420 has a first shielding plate 1421 and a second shielding plate 1422 which can clip on the outer surface and inner surface of upper or lower lip. The air conduit 1410 has a first opening connected to the lip interface 1420 and extends into the user's oral cavity. The air conduit 1410 also has a second opening which can be connected to a negative pressure source 100. The lip interface 1420 can be made of elastic material so that it can be attached and detached from the lip by pulling the first shielding plate 1421. The recoiling of the first shielding plate 1421 provides a holding force to securing the fluid conduit 1410. The lip interface 1420 has fluid passages 1430 connecting to the fluid conduit 1410 at one end and an array of holes 1431 on second shielding plate 1422. The array of holes 1431 is situated around the front teeth and can distribute negative pressure to the oral cavity. Once the lip interface 1420 is secured on with lip, the negative pressure source 100 can draw air out of the oral cavity through the array of holes 1431, the fluid passages 1430 and the fluid conduit 1410, and thus produce a negative pressure environment to pull the tongue, soft palate and other soft tissue forward to maintain the airway patency.

Figure 15A:
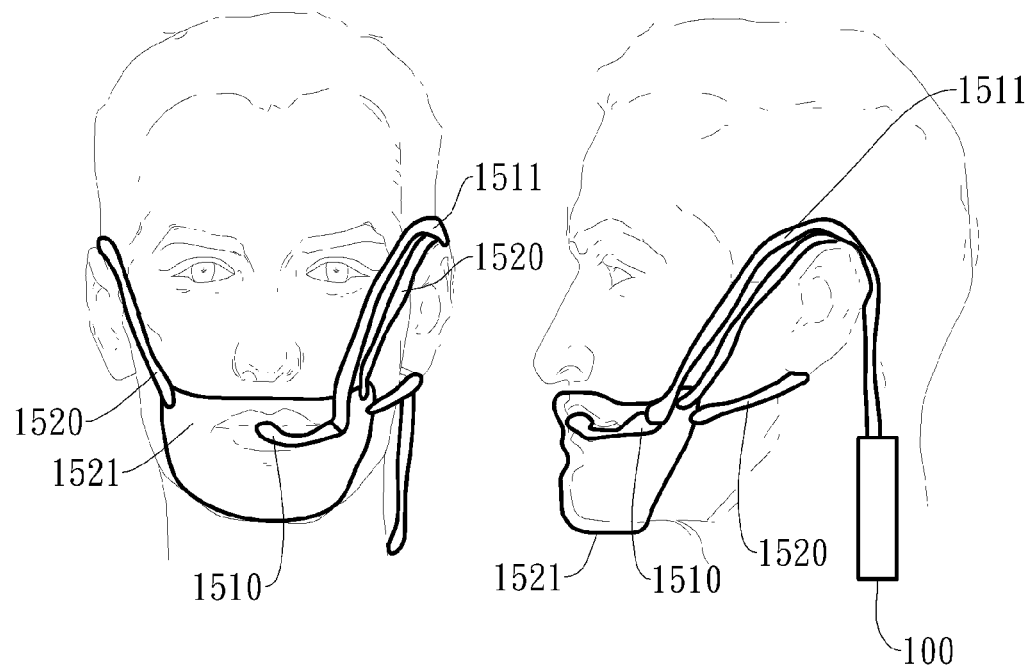
FIG. 15A show a schematic diagram of an oral apparatus according to the fifteenth embodiment of the present invention.

FIG. 15A shows front and side views of a negative pressure oral apparatus according to the fifteenth embodiment of the present invention. The negative pressure oral apparatus comprises of a fluid conduit 1510, a fluid conduit extension 1511, a fixation part which is a respirator mask 1521 and a strap(s) 1520. The respirator mask 1521 is integrated with the fluid conduit 1510 and covers both the mouth and the jaw. When tightly strapped to the user's head or ears, the respirator mask 1521 can prevent the mouth from opening and the jaw from dropping down. When the fluid conduit extension 1511 physically connects to a negative pressure source 100 at one end, and physically connects to the fluid conduit 1510 across the mask at the other end, the negative pressure source 100 can draw air out of the oral cavity, and thus produce a negative pressure environment to pull the tongue, soft palate and other soft tissue forward to maintain the airway patency.

Figure 15B:
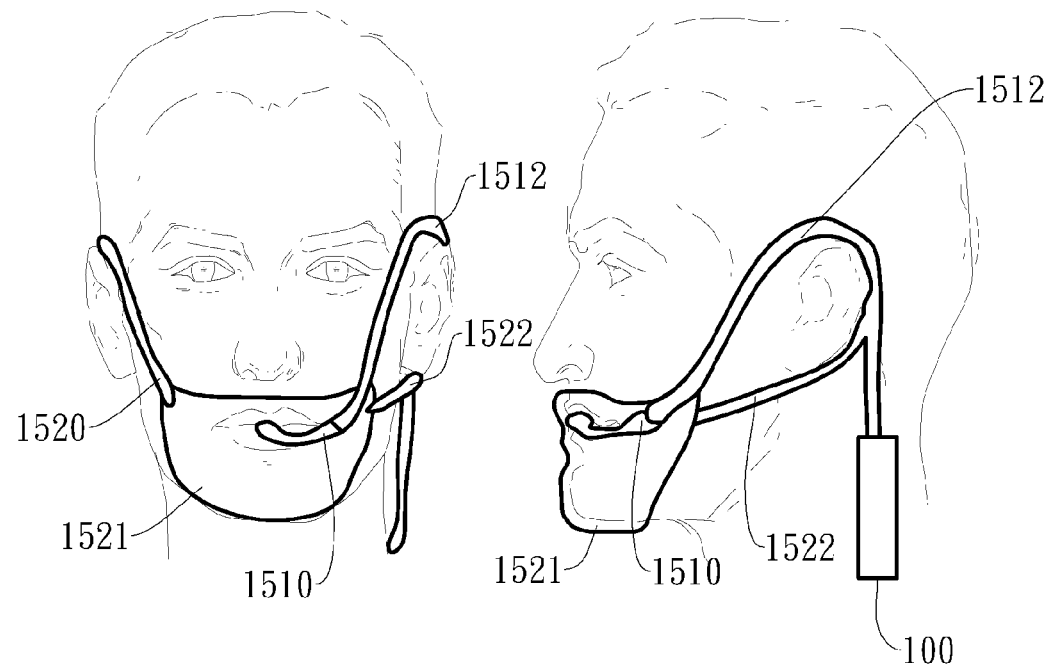
FIG. 15B shows a variation of the fifteenth embodiment of the present invention.

FIG. 15B shows front and side views of a variation of the fifteenth embodiment of the present invention. The negative pressure oral apparatus comprises of a fluid conduit 1510, a fluid conduit extension 1512, a respirator mask 1521, and straps 1520 and 1522. The respirator mask 1521 is integrated with fluid conduit 1510 and covers both the mouth and the jaw. The fluid conduit extension 1512 is integrated with the strap 1522 to provide more compact design and easier usage.

Figure 16A:
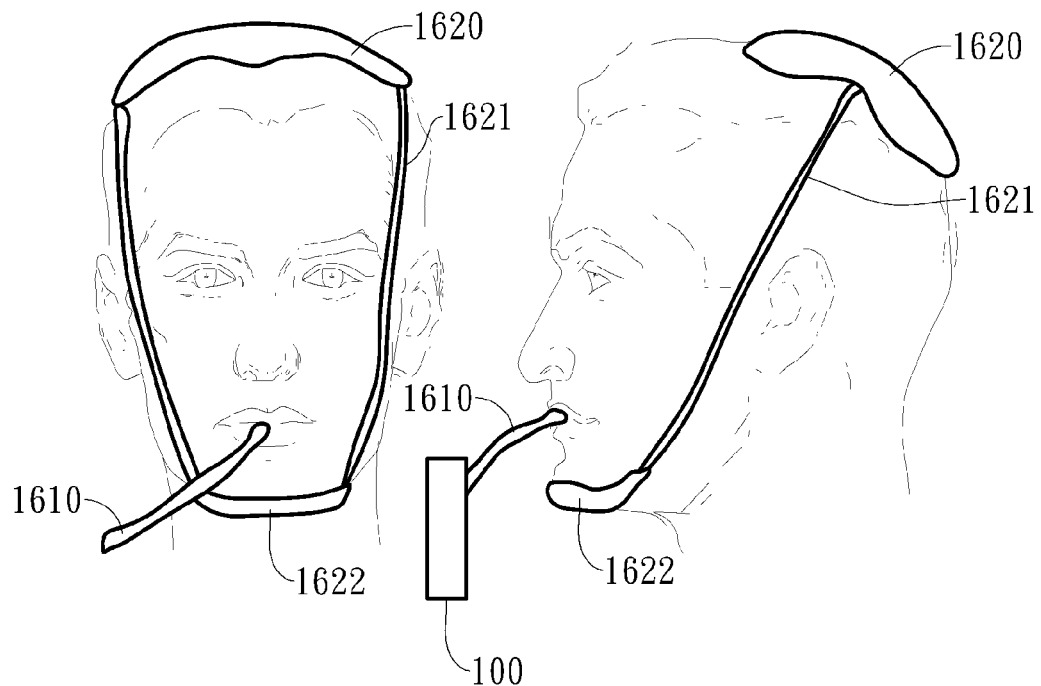
FIG. 16A shows a schematic diagram of an oral apparatus according to the sixteenth embodiment of the present invention.

FIG. 16A shows front and side views of a negative pressure oral apparatus according to the sixteenth embodiment of the present invention. The negative pressure oral apparatus comprises of a fluid conduit 1610 and a fixation part which comprises a head piece 1620 to fit on a user's head, a chin piece 1622 to support the user's lower jaw, and a strap(s) 1621 connecting the head piece 1620 and the chin piece 1622. The air conduit 1610 has a first opening extends into user's oral cavity and a second opening to be connected with a negative pressure source 100. The strap(s) 1621 can be fastened to a comfortable level to prevent the jaw from dropping down, and thus the mouth is closed. Once the fluid conduit 1610 are physically connected to a negative pressure source 100, the negative pressure source 100 can draw air out of the oral cavity, and thus produce a negative pressure environment to pull the tongue, soft palate and other soft tissue forward to maintain the airway patency.

Figure 16B:
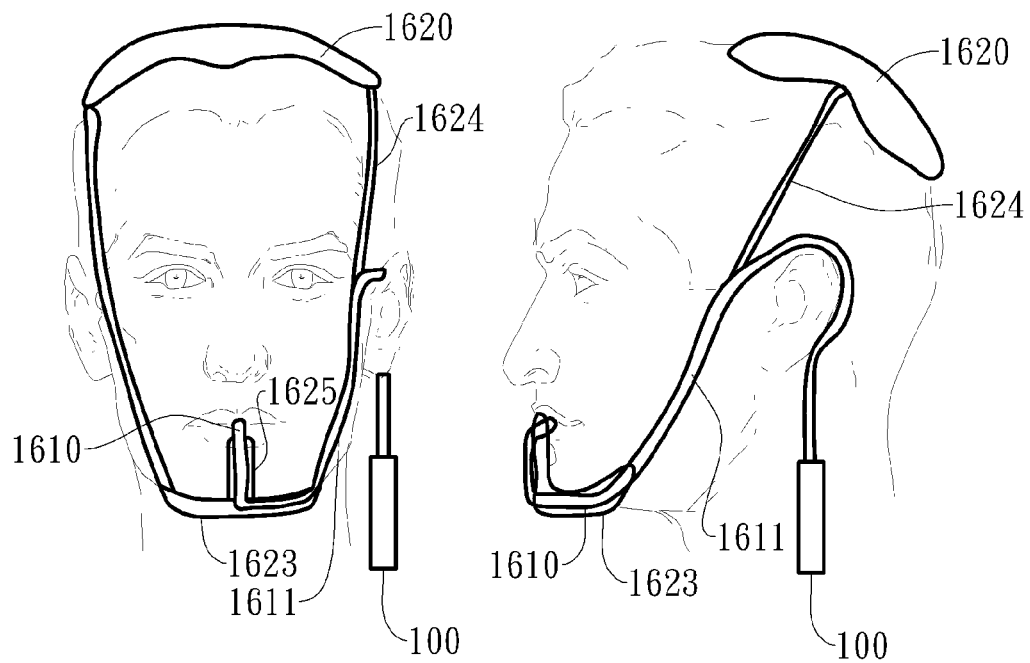
FIG. 16B shows a variation of the fifteenth embodiment of the present invention.

FIG. 16B shows front and side views of a variation of the sixteenth embodiment of the present invention. The negative pressure oral apparatus comprises of a fluid conduit 1610, a fluid conduit extension 1611, a head piece 1620, a chin piece 1623, and a strap(s) 1624 connecting the head piece 1620 and the chin piece 1623. The fluid conduit extension 1611 is integrated with the chin piece 1623 and the strap(s) 1624 to provide more compact design and easier usage. The chin piece 1623 may have a chin piece extension 1625 to support and secure the fluid conduit 1610. The strap(s) 1624 can be fastened to a comfortable level to prevent the jaw from dropping down, and thus the mouth is closed. Once the fluid conduit extension 1611 is physically connected to the fluid conduit 1610 at one end, and is physically connected to a negative pressure source 100 at the other end, a negative pressure source 100 can draw air out of the oral cavity, and thus produce a negative pressure environment to pull the tongue, soft palate and other soft tissue forward to maintain the airway patency.

It is to be understood that while this invention has been disclosed and illustrated with reference to particular embodiments, the principles involved are susceptible for use in numerous other embodiments that will be apparent to persons skilled in the art. This invention is, therefore, not to be limited to the specific forms or arrangement or parts described and shown.

What is claimed is:

1. A negative-pressure oral apparatus for generating a negative pressure within an oral cavity of a mouth of a user, comprising:
    a flow conduit having a first opening to fluidly connect with the user's oral cavity and a second opening to fluidly connect with a negative pressure source for generating the negative pressure in the oral cavity of the user;
    a first fixation part configured to be positioned within the mouth of the user, wherein the first fixation part is adapted to be coupled with the flow conduit;
    wherein the first fixation part comprises a tooth pairing part configured to engage and attach to only one or only two teeth of the user to prevent the flow conduit from falling out of the user's mouth; and
    a conduit pairing part with a shape complimentary to the tooth pairing part, wherein the conduit pairing part can physically connect and disconnect the flow conduit to the tooth pairing part.

2. The apparatus as claimed in claim 1, further comprising at least one second fixation part which is adapted to provide a secure connection to a second part of the user's body to facilitate closing of the user's mouth.

3. The apparatus as claimed in claim 2, wherein the apparatus comprises a pair of first fixation parts including a first tooth pairing part and a second tooth pairing part; and a pair of second fixation parts including a first conduit pairing part and a second conduit pairing part, and wherein the first conduit pairing part and the second conduit pairing part can mechanically or magnetically connect the first tooth pairing part and the second tooth pairing part to the first opening of the flow conduit, respectively, and help close the mouth.

4. The apparatus as claimed in claim 3, wherein the first conduit pairing part or the second conduit pairing part has a piston end which inserts into a cylinder end of the first opening of the flow conduit.

5. The apparatus as claimed in claim 2, wherein the first fixation part further comprises a first plate and a first slit fastening part; wherein the first opening of the flow conduit is connected to one face of the first plate; wherein the first slit fastening part extends from one end of the first plate to the other end of the first plate; wherein the first slit fastening part can be inserted into one or more slits between upper teeth; wherein the first plate can be held by the first slit fastening part against the surface of the upper teeth; wherein the second fixation part further comprises a second plate and a second slit fastening part; wherein the second slit fastening part can be inserted into one or more slits between lower teeth; wherein the second plate can be held by the second slit fastening part against the surface of the lower teeth.

6. The apparatus as claimed in claim 2, wherein the first fixation part further comprises a conduit-attachment plate and an adhesive film, the conduit-attachment plate has an opening which is connected to the first opening of the flow conduit, one surface of the first adhesive film adheres to one surface of the conduit-attachment plate, and the other surface of the first adhesive film adheres to a surface of the user's upper teeth; wherein the second fixation part further comprises an extending plate and a second adhesive film, one surface of the second adhesive film adheres to one surface of the extending plate, and the other surface of the first adhesive film adheres to a surface of the user's lower teeth.

7. The apparatus as claimed in claim 2, further comprising a lip interface sized and shaped such that it does not cover the entire mouth opening.

8. The apparatus as claimed in claim 7, further comprising a securing plate connected to the flow conduit and configured to be situated between the user's lips and teeth.

9. The apparatus as claimed in claim 2, wherein the first fixation part is a porous interface configured to be inserted into the user's oral cavity; wherein the second fixation part is an external shield connected with the flow conduit and configured to be attached to the skin near upper and lower lips to keep the user's mouth closed; wherein the external shield is sized and shaped such that it does not cover the entire region of mouth opening.

10. The apparatus as claimed in claim 2, wherein the first fixation part is a porous interface configured to be inserted into the user's oral cavity; wherein the second fixation part is an internal shield connected with the flow conduit and configured to be situated between lips and teeth; wherein the internal shield is sized and shaped such that it does not cover the entire region of mouth opening.

11. The apparatus as claimed in claim 2, wherein the first fixation part is a shielding porous interface connected to the flow conduit and configured to be situated between upper lip and upper teeth; wherein the second fixation part is an extending porous part configured to be situated between lower lip and lower teeth.

12. The apparatus as claimed in claim 2, wherein the first fixation part is a porous interface configured to be inserted into the user's oral cavity; wherein the second fixation part further comprises upper and lower shielding extensions configured to be situated between the user's lips and teeth.

13. The apparatus as claimed in claim 2, wherein the second fixation part is a respirator mask including a strap, the respirator mask is integrated with the flow conduit and configured to cover both the mouth and the jaw, the respirator mask configured to prevent the mouth from opening and the jaw from dropping down when tightly strapped to the user's head or ears.

14. The apparatus as claimed in claim 13, wherein the fluid conduit further comprises a flow conduit extension, the fluid conduit extension is integrated with the strap.

15. The apparatus as claimed in claim 2, wherein the second fixation part further comprises a head piece, a chin piece, and a strap connecting the head piece and the chin piece; wherein the strap can be fastened to a comfortable level to prevent the jaw from dropping down and help close the mouth.

16. The apparatus as claimed in claim 15, wherein the second fixation part further comprises a chin piece extension to support the flow conduit.

17. The apparatus as claimed in claim 15, further comprising a fluid conduit extension connected to the second opening of the flow conduit; wherein the fluid conduit extension is integrated with the chin piece and the strap.

18. The apparatus as claimed in claim 1, wherein the tooth pairing part and the conduit pairing part have any one of the following complimentary pairing structures: a disk-like fastening structure with a cylindrical space; or a rail-like fastening structure and a slot-like space.

19. The apparatus as claimed in claim 18, wherein the disk-like fastening structure of the tooth pairing part interlock with the cylindrical space of the conduit pairing part by rotation.

20. The apparatus as claimed in claim 18, wherein the rail-like fastening structure of the tooth pairing part interlock with the slot-like space of the conduit pairing part by sliding the pairing structure of the tooth pairing part into the matching space of the conduit pairing part.

21. The apparatus as claimed in claim 1, wherein the tooth pairing part is a paramagnetic or magnetic part and the conduit pairing part has a complementary magnetic or paramagnetic pairing structure.

22. The apparatus as claimed in claim 1, wherein the first fixation part further comprises a plate and a slit fastening part; wherein the first opening of the flow conduit is connected to one face of the plate; wherein the slit fastening part extends from one end of the plate to the other end of the plate; wherein the slit fastening part can be inserted into one or more slits between teeth; wherein the plate can be held by the slit fastening part against the surface of the teeth.

23. The apparatus as claimed in claim 22, further comprising a sliding part on the first opening of the flow conduit; wherein the slit fastening part passes through the plate and is connected to the sliding part; wherein the slit fastening part can be pulled by moving the sliding part to adjust contraction force on the teeth and fixed by friction force.

24. The apparatus as claimed in claim 22, wherein the plate may have one or more grooves on the surface facing the teeth to distribute the negative pressure.

25. The apparatus as claimed in claim 22, wherein the slit fastening part is a flexible T-shape slit fastening part; wherein the T-shape slit fastening part is stemmed from the center of the plate and can be stretched and inserted into a slit between teeth; wherein the T-shape slit fastening part further comprises an extending plate which applies contraction force on the other side of the user's teeth.

26. The apparatus as claimed in claim 25, further comprising a sliding part on the first opening of the flow conduit; wherein the slit fastening part passes through the plate and is connected to the sliding part; wherein the slit fastening part can be pulled by moving the sliding part to adjust contraction force on the teeth and fixed by friction force.

27. The apparatus as claimed in claim 1, wherein the first fixation part further comprises a conduit-attachment plate and an adhesive film, the conduit-attachment plate has an opening which is connected to the first opening of the flow conduit, one surface of the adhesive film adheres to one surface of the conduit-attachment plate, and the other surface of the adhesive film adheres to surface of the user's teeth.

28. The apparatus as claimed in claim 1, wherein the first fixation part is a flexible and/or porous tooth sheath which can cover at least one tooth; wherein the tooth sheath connects to the first opening of the flow conduit.

29. The apparatus as claimed in claim 1, wherein the first fixation part is a porous interface configured to be inserted into the user's oral cavity.

30. The apparatus as claimed in claim 1, wherein the tooth pairing part is configured to attach to the surface of the only one or only two teeth by gluing or bonding permanently or temporarily.

31. A method for generating a negative pressure within an oral cavity of a mouth of a user, comprising:
   providing a negative-pressure oral apparatus comprising a flow conduit and a first fixation part, the flow conduit having a first opening and a second opening;
   attaching a tooth pairing of the first fixation part to only one or only two teeth of the user such that the tooth pairing engages said only one or only two teeth;
   coupling the first fixation part with the first opening of the flow conduit so that the first fixation part provides a secure connection to the flow conduit to prevent the flow conduit from falling out of the user's mouth;
   connecting a negative pressure source to the second opening of the flow conduit, wherein the negative pressure source draws air out of the user's oral cavity; and producing negative pressure in the whole oral cavity using the negative-pressure oral apparatus and the negative pressure source to pull the tongue, soft palate and other soft tissue forward to maintain the airway patency.

32. The method as claimed in claim 31, further comprising attaching a second fixation part to a second part of the user's body to fix a relative position of the upper and lower lips, jaws, or teeth, wherein the second fixation part is sized and shaped such that it does not cover the entire mouth opening.

* * * * *